(12) United States Patent
Chen et al.

(10) Patent No.: US 8,781,243 B2
(45) Date of Patent: Jul. 15, 2014

(54) METHOD FOR CONSTRAINED RECONSTRUCTION OF HIGH SIGNAL-TO-NOISE RATIO IMAGES

(75) Inventors: Guang-Hong Chen, Madison, WI (US); Jie Tang, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 219 days.

(21) Appl. No.: 12/986,847

(22) Filed: Jan. 7, 2011

(65) Prior Publication Data
US 2012/0177267 A1 Jul. 12, 2012

(51) Int. Cl.
G06K 9/40 (2006.01)
G06K 9/00 (2006.01)

(52) U.S. Cl.
USPC ............................. 382/260; 382/131; 382/132

(58) Field of Classification Search
None
See application file for complete search history.

(56) References Cited

U.S. PATENT DOCUMENTS

| | | | |
|---|---|---|---|
| 4,878,169 A | | 10/1989 | Toner et al. |
| 5,594,767 A | * | 1/1997 | Hsieh ............................... 378/8 |
| 6,597,936 B1 | * | 7/2003 | Liu et al. ....................... 600/420 |
| 6,841,998 B1 | | 1/2005 | Griswold |
| 7,289,049 B1 | | 10/2007 | Fudge et al. |
| 7,330,027 B2 | | 2/2008 | Kozerke et al. |
| 7,358,730 B2 | | 4/2008 | Mistretta et al. |
| 7,408,347 B2 | | 8/2008 | Mistretta et al. |
| 7,519,412 B2 | | 4/2009 | Mistretta |
| 7,545,901 B2 | | 6/2009 | Mistretta |
| 7,558,414 B2 | | 7/2009 | Griswold |
| 7,646,924 B2 | | 1/2010 | Donoho |
| 7,647,088 B2 | | 1/2010 | Mistretta et al. |
| 2005/0169420 A1 | * | 8/2005 | Edic et al. ......................... 378/4 |
| 2007/0010731 A1 | | 1/2007 | Mistretta |
| 2007/0038073 A1 | | 2/2007 | Mistretta |
| 2007/0106149 A1 | | 5/2007 | Mistretta |
| 2007/0156044 A1 | | 7/2007 | Mistretta et al. |
| 2007/0167707 A1 | | 7/2007 | Mistretta et al. |
| 2007/0167728 A1 | | 7/2007 | Mistretta et al. |
| 2007/0167729 A1 | | 7/2007 | Mistretta et al. |
| 2008/0199063 A1 | | 8/2008 | O'Halloran et al. |
| 2008/0219535 A1 | | 9/2008 | Mistretta et al. |

(Continued)

OTHER PUBLICATIONS

Guy E. Lateur and Rik Van de Walle and Ignace L. Lemahieu, "Resampling MR signals in projection reconstruction MRI", (Apr. 25, 2000), Proc. SPIE, vol. 3977, 270-279.*

(Continued)

Primary Examiner — Atiba O Fitzpatrick
Assistant Examiner — Carol Wang
(74) Attorney, Agent, or Firm — Quarles & Brady, LLP (57) ABSTRACT

A method for producing an image having a high signal-to-noise ratio (SNR) is provided. An image to be enhanced is provided, the provided image including a previously reconstructed image or an image reconstructed from acquired image data. A prior image is produced from the provided image, for example, by filtering the provided image such that noise from the provided image is substantially suppressed in the prior image. Synthesized image data is produced by performing a forward projection of the provided image. A sparsified image is produced by subtracting the prior image and the provided image. A target image having a higher SNR than the provided image is reconstructed using the sparsified image, the provided image, and the synthesized image data. The provided image may be, for example, a medical image produced by an x-ray imaging system, including computed tomography and C-arm systems; a magnetic resonance imaging system; and the like.

14 Claims, 6 Drawing Sheets

(56) References Cited

U.S. PATENT DOCUMENTS

| | | | |
|---|---|---|---|
| 2009/0076369 A1 | 3/2009 | Mistretta | |
| 2009/0129651 A1 | 5/2009 | Zagzebski et al. | |
| 2009/0161932 A1* | 6/2009 | Chen | 382/131 |
| 2009/0161933 A1 | 6/2009 | Chen | |
| 2009/0175523 A1* | 7/2009 | Chen et al. | 382/130 |
| 2009/0232377 A1* | 9/2009 | Miao et al. | 382/131 |
| 2009/0274355 A1* | 11/2009 | Chen et al. | 382/131 |
| 2010/0183203 A1* | 7/2010 | Ye et al. | 382/128 |

OTHER PUBLICATIONS

Candes, et al., Robust Uncertainty Principles: Exact Signal Reconstruction from Highly Incomplete Frequency Information, IEEE Transactions on Information Theory, vol. 52, No. 2, Feb. 2006, 489-509.

Chen, Prior Image Constrained Compressed Sensing (PICCS); Proc Soc Photo Opt Instrum Eng, Mar. 3, 2008; 6856: 685618. doi:10.1117/12.770532.

Chen, Prior Image Constrained Compressed Sensing (PICCS): A Method to Accurately Reconstruct Dynamic CT Images from Highly Undersampled Projection Data Sets; Med. Phys., Feb. 2008; 35(2):660-663.

Donoho, Compressed Sensing, Sep. 14, 2004, pp. 1-34.

Donoho, Compressed Sensing, IEEE Transactions on Information Theory, vol. 52, No. 4, Apr. 2006, 1289-1306.

Fessler, et al., Iterative Image Reconstruction in MRI With Separate Magnitude and Phase Regularization, IEEE International Symposium on Biomedical Imaging: Nano to Macro, 2004; 1:209-212.

Lustig, et al., Rapid MR Imaging with 'Compressed Sensing' and Randomly Under-Sampled 3DFT Trajectories, Proc. Intl. Soc. Mag. Reson. Med. 14 (2006), p. 695.

Lustig, Student Member, IEEE, Compressed Sensing MRI, 18 pages, 2007.

Lustig, et al., Sparse MRI: The Application of Compressed Sensing for Rapid MR Imaging, Magnetic Resonance in Medicine 58:1182-1195 (2007).

Mistretta, et al., Highly Constrained Backprojection for Time-Resolved MRI, Magn Reson Med, 2006, 55(1):30-40.

Nett, et al., Tomosynthesis via Total Variation Minimization Reconstruction and Prior Image Constrained Compressed Sensing (PICCS) on a C-arm System; Proc Soc Photo Opt Instrum Eng, Mar. 18, 2008; 6913: nihpa92672. doi:10.1117/12.771294.

O'Halloran, et al., Iterative Projection Reconstruction of Time-Resolved Images Using Highly-Constrained Back-Projection (HYPR), Magn Reson Med, 2008, 59:132-139 (published online Dec. 3, 2007).

Schmidt, Least Squares Optimization with L1-Norm Regularization, Dec. 2005, pp. 1-12.

Song, et al., Sparseness Prior Based Iterative Image Reconstruction for Retrospectively Gated Cardiac Micro-CT, Med. Phys. 34(11), Nov. 2007, pp. 4476-4483.

* cited by examiner

METHOD FOR CONSTRAINED RECONSTRUCTION OF HIGH SIGNAL-TO-NOISE RATIO IMAGES

STATEMENT REGARDING FEDERALLY SPONSORED RESEARCH

This invention was made with United States government support under EB005712 awarded by the National Institutes of Health. The United States government has certain rights in this invention.

FIELD OF THE INVENTION

The field of the invention is imaging systems and methods, including medical imaging systems and methods. More particularly, the field of the invention is systems and methods for constrained image reconstruction that allow desirable levels of signal-to-noise ratio to be achieved without sacrificing spatial resolution.

BACKGROUND OF THE INVENTION

In medical imaging, as well as other imaging technologies, signal-to-noise ratio ("SNR") is utilized as a quantitative measure of image quality. Generally, SNR is defined as the ratio between the mean intensity value and the root-mean-square ("RMS") noise, σ, in an image. The term "net signal" refers to the difference between an average signal value over the image, and background values, whereas the term RMS noise refers to the standard deviation of the noise value in the image. As SNR decreases in a medical image, it becomes increasingly more difficult to differentiate between anatomical features and other clinical findings of importance to the clinician. Thus, it is generally desirable to provide a relatively high SNR in medical imaging applications.

Spatial resolution is typically balanced with respect to the achievable SNR in an image. For example, the traditional relationship between spatial resolution, $\Delta x$, in a two-dimensional image and the achievable SNR in that image is given by:

$$\sigma^2 \propto \frac{1}{\Delta x^3}. \quad \text{(1)}$$

Thus, as spatial resolution becomes finer, the noise variance, $\sigma^2$, present in the image increases significantly. The SNR characteristics of an image are also governed by the manner in which image data is initially acquired. In many instances, it may be beneficial to alter data acquisition parameters, such as decreasing radiation dose or scan time, to the betterment of the subject of the examination, but to the detriment of SNR in the resultant images.

When parameters of an x-ray imaging study, such as tube current and tube current time product, "mAs," are varied in order to decrease the radiation dose imparted to the subject, the SNR of the resultant images suffers. For example, decreasing tube current produces a related decrease in radiation dose; however, the noise present in the resultant images is increased, thereby affecting SNR in accordance with the following relationship:

$$SNR = \frac{\mu}{\sigma} \propto \sqrt{\text{Dose}} \propto \sqrt{mAs}; \quad \text{Eqn. (2)}$$

where $\mu$ is the measured linear attenuation coefficient and $\sigma$ is the RMS noise. Thus, if mAs is reduced by half, SNR will decrease by a factor of $\sqrt{1/2}$, which corresponds to about a thirty percent decrease in SNR. Thus, while decreasing mAs during an x-ray imaging study provides a beneficial decrease in radiation dose imparted to the subject being imaged, the resultant images suffer from increased noise and, therefore, decreased SNR. Such images have limited clinical value.

Depending on the technique used, many magnetic resonance imaging ("MRI") scans currently require many minutes to acquire the necessary data used to produce medical images. The reduction of this scan time is an important consideration, since reduced scan time increases patient throughout, improves patient comfort, and improves image quality by reducing motion artifacts. Many different strategies have been developed to shorten the scan time, including so-called parallel MRI ("pMRI") techniques.

While the use of parallel MRI acts to decrease the amount of time required to image a subject without increasing gradient switching rates or RF power, parallel MRI methods are plagued with losses in signal-to-noise ratio ("SNR"). In general, the SNR of an image reconstructed using parallel MRI methods is decreased in accordance with the following relationship:

$$SNR \propto \frac{1}{g\sqrt{R}}; \quad \text{Eqn. (3)}$$

where g is the so-called geometry factor, or "g-factor," and R is the acceleration factor, which describes the degree of undersampling employed and is related to, and generally limited by, the number of receiver coils in the array. Thus, parallel MRI methods suffer from a reduction in achievable SNR, offsetting the benefits provided by decreased scan time requirements.

It would therefore desirable to provide a method for image reconstruction or image processing in which an image having high SNR and high spatial resolution can be produced.

SUMMARY OF THE INVENTION

The present invention overcomes the aforementioned drawbacks by providing a method for producing an image having a high signal-to-noise ratio (SNR) by imparting the high SNR characteristics of a low spatial or temporal resolution prior image to a target image. An image to be enhanced is provided, the provided image including a previously reconstructed image or an image presently reconstructed from acquired image data. A prior image is produced from the provided image, for example, by filtering the provided image such that noise from the provided image is substantially suppressed in the prior image. Synthesized image data is produced by performing a forward projection of the provided image. A sparsified image is produced by subtracting the prior image and the provided image. A target image having a higher SNR than the provided image is reconstructed using the sparsified image, the provided image, and the synthesized image data. The provided image may be, for example, a medical image produced by at least one of an x-ray imaging system, an x-ray computed tomography system, a C-arm x-ray imaging system, an x-ray tomosynthesis imaging system, an x-ray projection imaging system, a magnetic resonance imaging system, a positron emission tomography system, a single photon emission computed tomography system, an ultrasound imaging system, and an optical imaging system.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Generally speaking, the method of reconstructing an image from a set of data includes a series of numerical steps to estimate a target image, I, from the measured data samples, Y. More specifically, the image reconstruction should fulfill the following consistency condition:

$$AI = Y \quad (4);$$

where A is a system matrix. In general, the system matrix, A, can be viewed as a forward projection operator that relates the target image, I, to the acquired data samples, Y. When dealing with computed tomography ("CT") imaging, the system matrix can include a reprojection operation, while in magnetic resonance imaging ("MRI"), it can include a Fourier transform operation. The consistency condition of Eqn. (4), put in other words, states that when an image is faithfully reconstructed, the forward operation should substantially mimic the actual data acquisition procedure in order to generate a correct estimate of the measured projection data.

A method for reconstructing a quality desired, or target, image is provided herein. In general, a so-called "prior image" is employed to constrain an iterative image reconstruction method, in which the principles of compressed sensing ("CS") are utilized. For example, in addition to the sparsifying transforms commonly used in CS, an image is further sparsified by subtracting the prior image from the target image. In this manner, the image reconstruction method is referred to as prior image constrained compressed sensing, or "PICCS." Using PICCS, an image can be accurately reconstructed using a substantially fewer number of samples than required by CS methods. Additionally, it is a discovery that the noise characteristics from the prior image are imparted to the target image that is reconstructed.

Given a prior image, $I_P$, and a target image to be reconstructed, I, the PICCS image reconstruction method may be implemented by minimizing the following objective function:

$$\alpha \|\Psi_1(I-I_P)\|_1 + (1-\alpha)\|\Psi_2 I\|_1 \quad (5);$$

where $\Psi_1$ and $\Psi_2$ are sparsifying transforms, $\|\ldots\|_1$ is an $L_1$-norm operation, and $\alpha$ is a weighting parameter that is utilized to control the relative weight of the two terms in the objective function of Eqn. (5). The data consistency condition presented in Eqn. (4) is imposed during the minimization of the objective function presented in Eqn. (5). It is noted that the $L_1$-norm operation has the form:

$$\|x\|_1 = \sum_{i=1}^{N} |x_i|; \quad (6)$$

for an N-dimensional vector, x. More generally, a deviation from the true $L_1$-norm is possible while still maintaining adequate image quality in the target image. For example, the objective function of Eqn. (5) can be generalized as:

$$\alpha \|\Psi_1(I-I_P)\|_p^p + (1-\alpha)\|\Psi_2 I\|_p^p, \quad (7);$$

where $\|\ldots\|_p$ is an $L_p$-norm operation having the form:

$$\|x\|_p = \left(\sum_{i=1}^{N} |x_i|^p\right)^{1/p}. \quad (8)$$

As noted above, preferably, p=1.0; however, in the alternative, different values of p are possible. It should be appreciated by those skilled in the art that the further the value of p deviates from p=1.0, generally, the more degradation will be evident in the reconstructed target image.

The sparsifying transforms, $\Psi_1$ and $\Psi_2$, in Eqn. (5) are, in general, different; however, in the alternative, $\Psi_1$ and $\Psi_2$ may be the same sparsifying transform. Exemplary sparsifying transforms include a wavelet transform, a first order finite difference, a second order finite difference, and a discrete gradient transform, such as, for example, a discrete gradient transform, $\nabla_{m,n}$, having the following form:

$$\nabla_{m,n} I(m,n) = \sqrt{(I(m+1,n)-I(m,n))^2 + (I(m,n+1)-I(m,n))^2} \quad (9);$$

where the indices m and n indicate the location of a pixel in an image, I. The image specified as $\nabla_{m,n} I(m,n)$ is commonly referred to as the "gradient image."

Both of the terms in the objective function of Eqn. (5) are important. As a result of their importance, the selection of the weighting parameter, $\alpha$, is utilized to control the overall image reconstruction process. Therefore, the selection of the weighting parameter, $\alpha$, will depend on the choice of the prior image, $I_P$, and also the clinical application at hand. For example, the second term in the objective function of Eqn. (5), $(1-\alpha)\|\Psi_2 I\|_1$, mitigates streaking, or other, artifacts that are potentially inherited from the prior image, $I_P$. By way of further example, selecting a weighting parameter of $\alpha \approx 0.3$-$0.7$ is generally sufficient for cardiac imaging applications.

To better incorporate the consistency condition of Eqn. (4) into the overall image reconstruction, the method of Lagrange multipliers may be utilized. In such a manner, the consistency condition is employed to add a further constraint on the minimization of the objective function set forth in Eqn. (5). A new objective function is thus produced, which has the form:

$$\alpha\|\Psi_1(I-I_P)\|_1+(1-\alpha)\|\Psi_2 I\|_1+\lambda\|X\|_2^2 \quad (10);$$

where $\lambda$ is the Lagrange multiplier, X is a difference matrix defined below in Eqn. (12), and $\|\ldots\|_2^2$ is a squared $L_2$-norm operation, which, for an N-dimensional vector, x, has the form:

$$\|x\|_2^2 = \sum_{i=1}^{N} x_i^2. \quad (11)$$

The difference matrix in Eqn. (10) accounts for the consistency condition of Eqn. (4), and has the following form:

$$X=AI-Y \quad (12).$$

It is noted, again, that the $L_1$-norm operations in Eqn. (10) can similarly be replaced with the more general $L_p$-norm operations, as discussed above. The Lagrange multiplier, $\lambda$, is determined empirically for the particular imaging system employed when practicing the present invention. For example, the Lagrange multiplier, $\lambda$, is determined by a predetermined tradeoff between the target data consistency requirement and the similarity to the prior image, $I_p$. When a large Lagrange multiplier, $\lambda$, is selected, the reconstructed image has lower noise variance; however, this may be achieved as a loss of the high spatial resolution characteristic of the prior image. Similarly, when a smaller Lagrange multiplier, $\lambda$, is used, the high spatial resolution characteristic of the prior image is well preserved, but the noise variance can be high in the target image. Such a situation affects the contrast-to-noise ratio achievable by the imaging system utilized. As will be described below in detail, however, a large Lagrange multiplier, $\lambda$, need not be employed to provide an increase, or maintenance of an existing desirable level of, signal-to-noise ratio ("SNR"). Instead, a high SNR prior image, $I_p$, may be produced and the SNR of this prior image is imparted to the target image, I.

The objective function presented in Eqn. (10) can further be altered in order to account for noise characteristics of the imaging system. In such a manner, the following objective function is minimized:

$$\alpha\|\Psi_1(I-I_P)\|_1+(1-\alpha)\|\Psi_2 I\|_1+\lambda(X^T D X) \quad (13);$$

where $X^T$ is the transpose of the difference matrix, X, and D is a system noise matrix, which is a diagonal matrix having the following matrix elements:

$$D_{ij} = \begin{cases} \frac{1}{\sigma_n^2} & \text{if } i=j \\ 0 & \text{if } i \neq j, \end{cases} \quad (14)$$

where $\sigma_n^2$ an is the noise variance, and is a parameter indicative of noise in the imaging system employed when practicing the present invention. For example, in an x-ray imaging system, the noise parameter, $\sigma_n^2$, is the noise variance associated with the $n^{th}$ x-ray detector. Alternatively, in an MR imaging system, the noise parameter, $\sigma_n^2$, is estimated noise variance in the $n^{th}$ receiver coil. Again, the $L_1$-norm operations in Eqn. (13) may similarly be replaced with the more general $L_p$-norm operations.

In PICCS image reconstruction methods, the prior image, $I_P$, plays several roles. First, it serves as a seed image in the iterative reconstruction, which accelerates the overall image reconstruction method. Second, the prior image, $I_P$, is employed to further sparsify the target image, I, and, thus, serves as yet another sparsifying transform. In addition, as will be described below in detail, the SNR of the prior image, $I_P$, is imparted to the target image, I, thereby allowing the reconstruction of a target image, I, having both a high SNR and high spatial resolution.

A brief discussion of possible prior images, $I_P$, is provided below with respect to different imaging modalities; however, it should be appreciated by those skilled in the art that prior images, $I_P$, other than those expressly described herein can be employed depending on the clinical application. As referred to herein, a prior image, $I_P$, is an image of the subject that includes a priori information indicative of the target image to be reconstructed. Generally, the prior image, $I_P$, is formed from a previously performed imaging study. For example, and as will be described in detail below, the prior image, $I_P$, may be formed by filtering a preexisting image of the subject under examination. Exemplary filtering may include low pass filtering, resulting in a prior image, $I_P$, having low noise and low spatial resolution characteristics. As will be described below, the low noise of the prior image, $I_P$, is imparted to the target image of the subject, while the spatial resolution of the target image is determined not by the prior image, $I_P$, but by characteristics of the image data utilized to reconstruct the target image.

Figure 1:
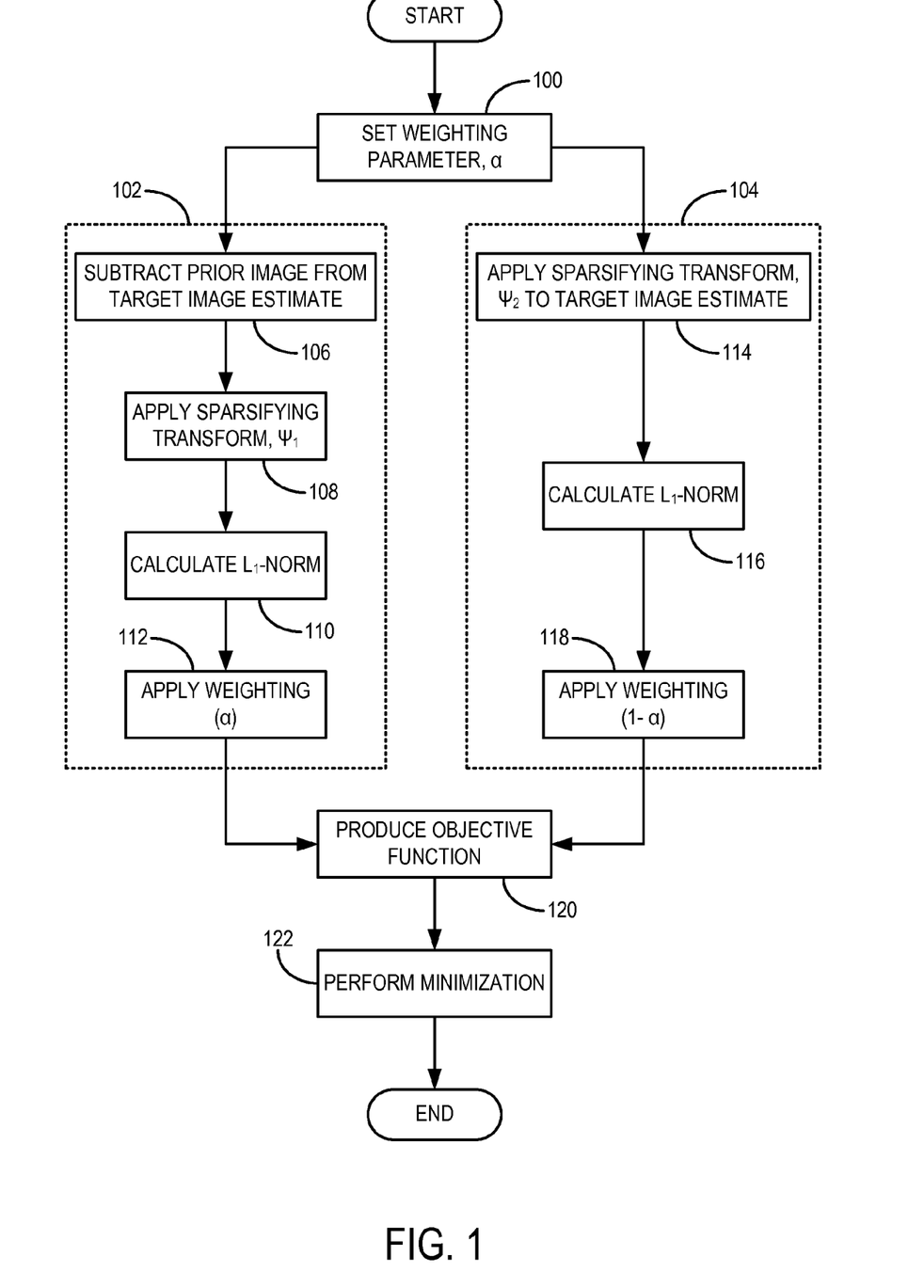
FIG. 1 is a flowchart setting forth the steps of an exemplary image reconstruction method employed when practicing the present invention.

With reference now to FIG. 1, one implementation of a PICCS image reconstruction employs the objective function of Eqn. (5), and begins by initializing the weighting parameter, $\alpha$, as indicated at step 100. The choice of the weighting parameter, $\alpha$, determines the trade-off between the sparsity of the target image, and the influence of the prior image on the target image. Accordingly, the value of the weighting parameter, $\alpha$, will vary depending on the clinical application at hand. For example, a value of $\alpha \approx 0.3$-$0.7$ is generally sufficient for cardiac imaging applications. Subsequently, the first and second terms in the objective function of Eqn. (5) are initialized, as indicated in steps 102 and 104, respectively. The initialization of the first term, $\alpha\|\Psi_1(I-I_P)\|_1$, begins at step 106 where the prior image, $I_P$, is subtracted from an estimate of the target image, I, to produce a "difference image." The particular choice of the prior image, $I_P$, and the estimate of the target image, I, will depend on the imaging modality and the particular clinical application. Accordingly, different alternatives for these choices will be discussed in detail below. The difference image is subsequently sparsified by applying the sparsifying transform, $\Psi_1$, as indicated at step 108. As described above, the sparsifying transform, $\Psi_1$, can be any number of mathematical operations, including a wavelet transform, a first order finite difference, a second order finite difference, and a discrete gradient transform. In some instances, the sparsifying transform, $\Psi_1$, may also include an identity matrix. The $L_1$-norm of this sparsified difference image is then calculated at step 110. The result of this process is then weighted by the weighting parameter, $\alpha$, as indicated at step 112.

The initialization of the second term in the objective function of Eqn. (5), $(1-\alpha)\|\Psi_2 I\|_1$, begins at step 114 where the estimate of the target image, I, is sparsified through the application of the sparsifying transform, $\Psi_2$. Subsequently, the $L_1$-norm of this sparsified target image estimate is calculated at step 116. When the discrete gradient transform, $\nabla_{m,n}$, is selected as the sparsifying transform, $\Psi_2$, steps 114 and 116 can be viewed as calculating the total variation, TV, of the target image estimate, which has the form:

$$TV(I) = \|\nabla I\|_1 = \Sigma |\nabla I| \tag{15}$$

After the $L_1$-norm of the sparsified target image estimate is calculated, the result is weighted by $(1-\alpha)$, as indicated at step 118. The objective function of Eqn. (5) is subsequently produced in step 120 by adding the first and second terms together. This objective function is then minimized, as indicated at step 122, using, for example, a nonlinear conjugate gradient method. The minimization process proceeds until a stopping criterion is satisfied. The stopping criterion includes, for example, comparing the current estimate of the target image with the estimate of the target image from the previous iteration. Such a stopping criterion has the following form:

$$\sum_i \sum_j (I_{ij}^{(k+1)} - I_{ij}^{(k)})^2; \tag{16}$$

where, $I_{ij}^{(k+1)}$ is the value of the $(k+1)^{th}$ estimate of the target image at the pixel location $(i,j)$, and $I_{ij}^{(k)}$ is the value of the $k^{th}$ estimate of the target image at the pixel location $(i,j)$.

Figure 2:
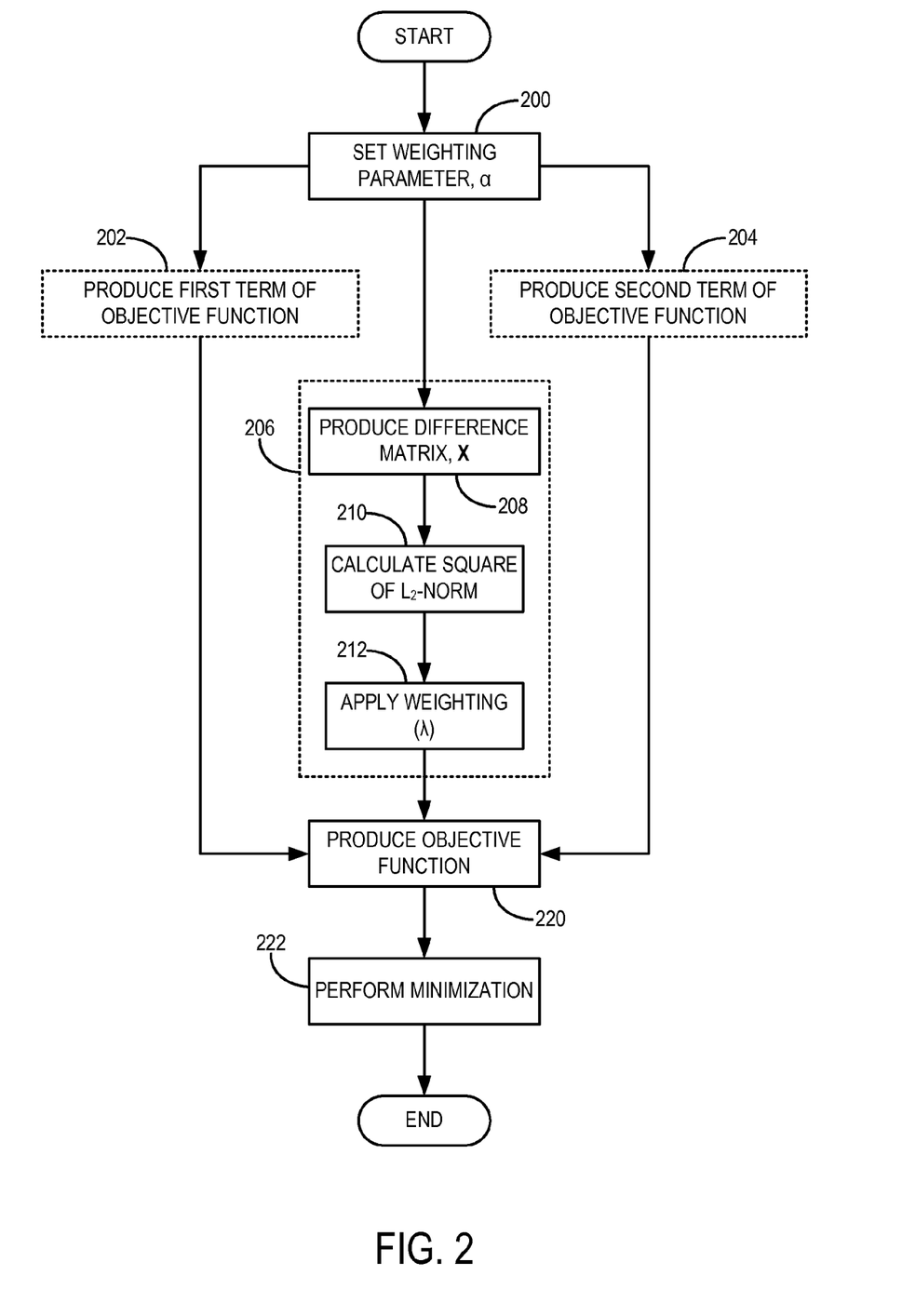
FIG. 2 is a flowchart setting forth the steps of another exemplary image reconstruction method employed when practicing the present invention.

With reference now to FIG. 2, another implementation of a PICCS image reconstruction employs the objective function of Eqn. (10), and begins by initializing the weighting parameter, $\alpha$, as indicated at step 200. Subsequently, the first and second terms in the objective function of Eqn. (10) are initialized, as indicated in steps 202 and 204, respectively. This process proceeds in the same manner as described above with reference to steps 102 and 104 in FIG. 1. Now, however, the consistency condition of Eqn. (4) is incorporated into a third term, $\lambda \|X\|_2^2$, which is initialized at step 206. First, the difference matrix, X, is produced, as indicated at step 208. As described above in detail, the difference matrix, X, is related to the consistency condition of Eqn. (4) and has the following form:

$$X = AI - Y \tag{17}$$

Thus, the difference matrix is determined by applying the system matrix, A, to the estimate of the target image, I, and subsequently subtracting the acquired image data, Y, that corresponds to the target image. The square of the $L_2$-norm of the difference matrix, X, is calculated next at step 210. After the square of the $L_2$-norm of the difference matrix, X, has been produced, the Lagrange multiplier, $\lambda$, is determined and employed to weight the difference matrix, X, as indicated at step 212. As described above, the Lagrange multiplier is empirically determined by a value selected by the user based on the clinical application at hand. The objective function of Eqn. (10) is subsequently produced in step 220 by adding the first, second, and third terms together. This objective function is then minimized, as indicated at step 222, using, for example, a nonlinear conjugate gradient method. The minimization process proceeds until a stopping criterion is satisfied, as described above.

Figure 3:
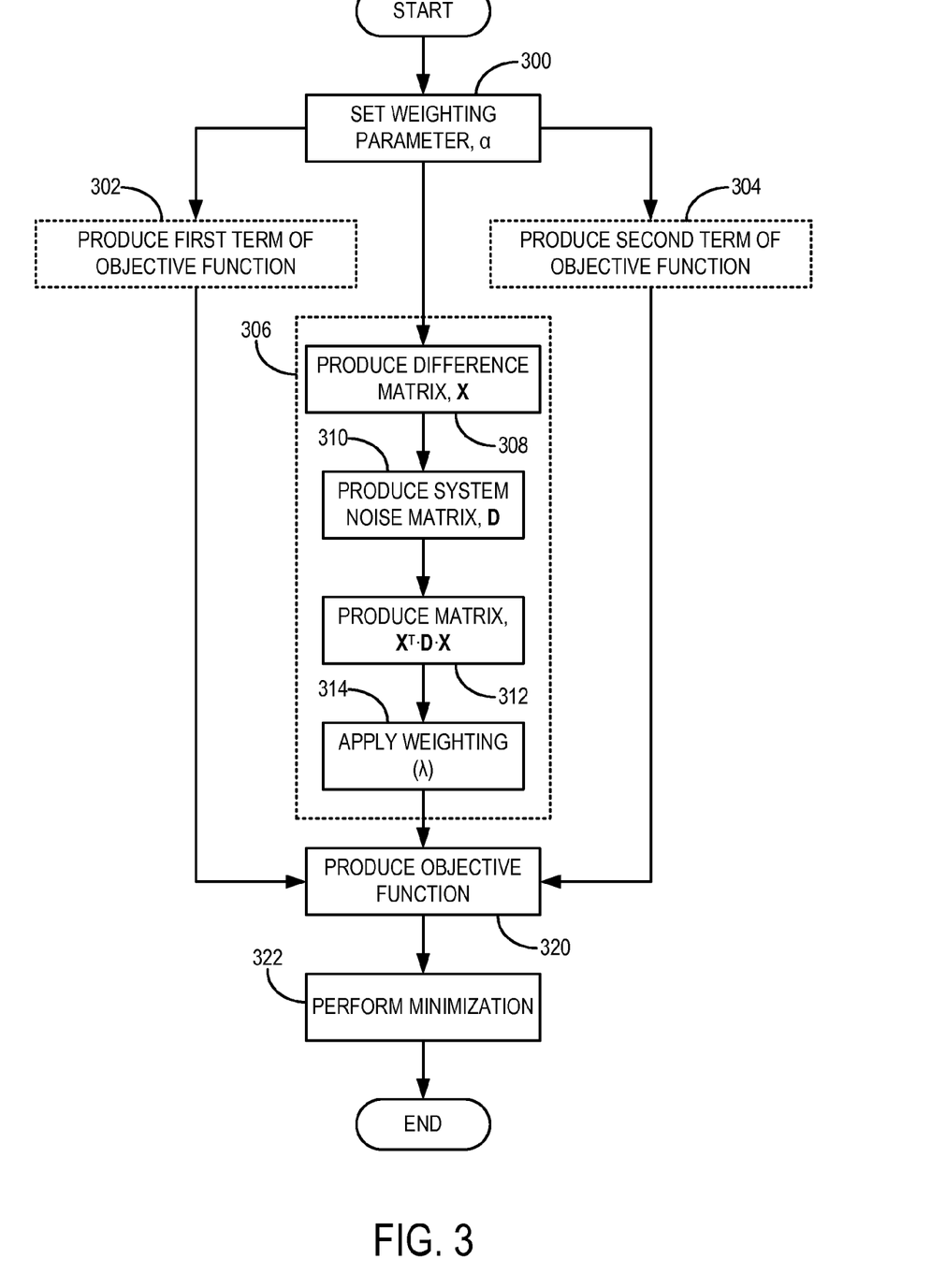
FIG. 3 is a flowchart setting forth the steps of yet another exemplary image reconstruction method employed when practicing the present invention.

With reference now to FIG. 3, yet another implementation of a PICCS image reconstruction employs the objective function of Eqn. (13), and begins by initializing the weighting parameter, $\alpha$, as indicated at step 300. Subsequently, the first and second terms in the objective function of Eqn. (13) are initialized, as indicated in steps 302 and 304, respectively. This process proceeds in the same manner as described above with reference to steps 102 and 104 in FIG. 1. Now, however, the consistency condition of Eqn. (4) and the effects of noise in the imaging system are incorporated into a third term, $\lambda(X^T DX)$, which is initialized at step 306. First, the difference matrix, X, is produced, as indicated at step 308, and described above with reference to step 208 in FIG. 2. Next, a system noise matrix, D, is produced, as indicated in step 310. The system noise matrix, D, is a diagonal matrix having matrix elements determined in accordance with the following:

$$D_{ij} = \begin{cases} \frac{1}{\sigma_n^2} & \text{if } i = j \\ 0 & \text{if } i \neq j. \end{cases} \tag{18}$$

As described above, $\sigma_n^2$ is the noise variance, which is a parameter indicative of noise in the imaging system employed to acquire the relevant image data. For example, in an x-ray imaging system, the noise parameter, $\sigma_n^2$, may be the noise variance associated with the $n^{th}$ x-ray detector. Alternatively, in an MRI system, the noise parameter, $\sigma_n^2$, may be the estimated noise variance in the $n^{th}$ receiver coil. After the system noise matrix, D, has been produced, the following matrix multiplication is performed:

$$X^T DX \tag{19};$$

as indicated at step 312. The result of this operation is subsequently scaled by the Lagrange multiplier, as indicated at step 314. The objective function of Eqn. (13) is subsequently produced in step 320 by adding the first, second, and third terms together. This objective function is then minimized, as indicated at step 322, using, for example, a nonlinear conjugate gradient method. The minimization process proceeds until a stopping criterion is satisfied, as described above.

With the appropriate choice of a prior image, $I_p$, a target image, I, can be reconstructed with both high SNR and spatial resolution. In general, the SNR of the prior image, $I_p$, is imparted to the target image, I, by way of the aforementioned PICCS image reconstruction methods. Therefore, consideration of how the prior image, $I_p$, is produced can provide benefits to the overall image quality of the target image, I. For example, the quality of preexisting medical images can be improved by forming a low noise, low spatial resolution prior image from the existing images and appropriately resampling the existing images to produce image data from which higher quality target images may be reconstructed.

It is noted that the present invention provides an image reconstruction method applicable to a number of different imaging modalities including x-ray computed tomography ("CT"), x-ray C-arm imaging, x-ray tomosynthesis imaging, magnetic resonance imaging ("MRI"), positron emission tomography ("PET"), single photon emission computed tomography ("SPECT"), optical imaging, and ultrasound imaging. More specifically, the present invention provides an image reconstruction method that provides an increase in achievable signal-to-noise ratio ("SNR") in reconstructed images, without a significant decrease in spatial resolution. This method is also applicable for post-processing applications, in which the SNR of an existing image is enhanced. Additionally, the method is applicable to other imaging modalities, including optical imaging using light in both the visible and other spectral ranges.

As described above, the presently described constrained image reconstruction method is applicable to many different medical imaging modalities and may be utilized in many different clinical applications. A number of such exemplary clinical applications are described below to illustrate the broad scope of the present invention. Such embodiments do not necessarily represent the full scope of the invention, however, and reference is made therefore to the claims and herein for interpreting the scope of the invention.

Figure 4:
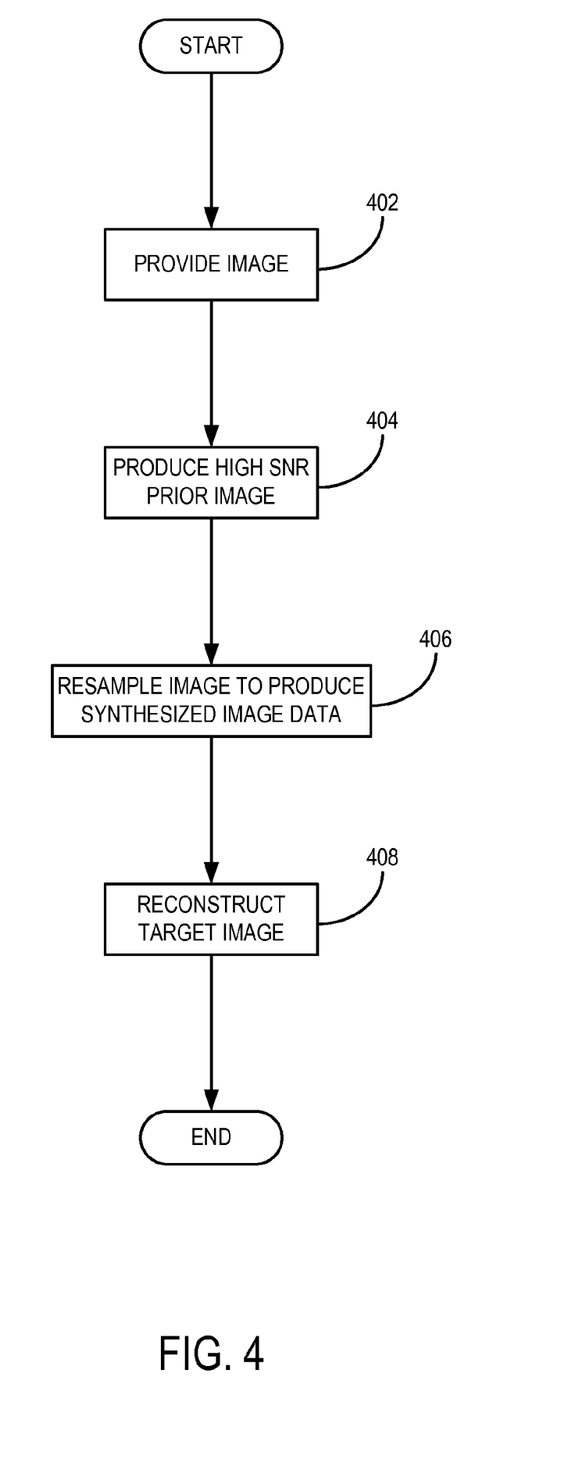
FIG. 4 is a flowchart setting forth the steps of an exemplary image reconstruction method in which an image having higher signal-to-noise ratio than a provided image is produced using the provided image.

Referring now to FIG. 4, a flowchart setting forth the steps of an exemplary image reconstruction method in which the signal-to-noise ratio ("SNR") of an existing image is enhanced to produce a high resolution, high SNR target image is illustrated. The method begins by providing an image from which a target image having an improved SNR is to be produced, as indicated at step 402. For example, an image having poor SNR is provided. A prior image is produced from this provided image, as indicated at step 404. The prior image is produced by filtering the provided image so that the noise is in the provided image is substantially suppressed. This process, however, also degrades the spatial resolution of the provided image. Exemplary filtering includes the application of a low pass filter, or the like. Similarly, a smoothing filter, such as Gaussian smoothing filter, can be applied to the provide image to produce a low noise prior image; however, such an approach also removes information related to the texture of the original noise, which may be undesirable in some applications.

When the acquired image data from which the provided image was originally reconstructed is not available, the provided image is resampled, for example by forward projection, to produce synthesized image data, as indicated at step 406. The choice of resampling kernel may vary depending on the desired clinical application and on considerations of transform domain characteristics. Exemplary resampling kernels include those that transform the provided image into x-ray projection space, for example by Radon transform; k-space, for example by Fourier transform; and a wavelet transform domain, for example by wavelet transform. In some instances, the provided image may also be resampled in the image domain prior to performing a forward projection. For example, the provided image may be oversampled to increase its spatial resolution. This oversampling provides an additional guarantee that the spatial resolution is properly encoded in the synthesized image data. Because the provided image is resampled in this manner, it does not matter how the provided image was originally acquired. Therefore, the image reconstruction method is "universal," in as much as it is applicable to any such previously obtained image.

Using the produced prior image and the synthesized image data, a high spatial resolution, high SNR target image is reconstructed using a prior image constrained compressed sensing ("PICCS") reconstruction technique, as indicated at step 408. As noted, the reconstructed target image depicts the same subject as the provided image, but contains a higher SNR by virtue of the high SNR prior image, and similar or increased spatial resolution by virtue of the synthesized image data. Exemplary image reconstruction includes the minimization of an objective function that includes terms related to the prior image and synthesized image data. For example, the objective function in Eqn. (7) may be modified as follows:

$$\alpha\|\Psi_1(I-I_P)\|_p^p+(1-\alpha)\|\Psi_2 I\|_p^p+\lambda\|RI-RI_0\|_2^2 \quad (20);$$

where R is a resampling operator, such as those discussed above, and may in some instances be selected as an identity matrix; $I_0$ is the provided image; and $RI_0$ is the synthesized data. When R is selected as the identity matrix, the implication is to allow the forward projection of the target image, I, and of the provided image, $I_0$, to equal their respective selves. In such an instance, the objective function provided in Eqn. (20) may be rewritten as:

$$\alpha\|\Psi_1(I-I_P)\|_p^p+(1-\alpha)\|\Psi_2 I\|_p^p+\lambda\|I-I_0\|_2^2 \quad (21).$$

Figure 5A:
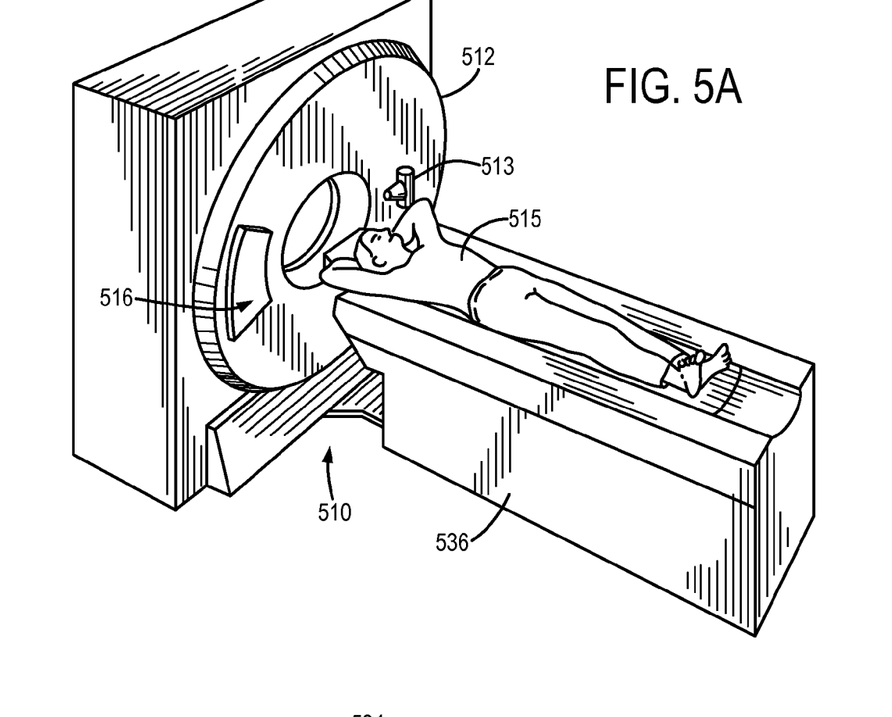
FIG. 5A is a pictorial view of an exemplary x-ray computed tomography ("CT") imaging system.

Thus, the image reconstruction method can be used to the advantage of enhancing preexisting images as well as guiding future data acquisitions. For example, an x-ray computed tomography data acquisition can be altered such that a lower x-ray radiation dose is imparted to the subject. In this instance the SNR of an image reconstructed from such lower dose image data would With initial reference to FIGS. 5A and 5B, an x-ray computed tomography ("CT") imaging system 510 includes a gantry 512 representative of a "third generation" CT scanner. Gantry 512 has an x-ray source 513 that projects a fan-beam, or cone-beam, of x-rays 514 toward a detector array 516 on the opposite side of the gantry. The detector array 516 is formed by a number of detector elements 518 which together sense the projected x-rays that pass through a medical patient 515. Each detector element 518 produces an electrical signal that represents the intensity of an impinging x-ray beam and hence the attenuation of the beam as it passes through the patient. During a scan to acquire x-ray projection data, the gantry 512 and the components mounted thereon rotate about a center of rotation 519 located within the patient 515.

Figure 5B:
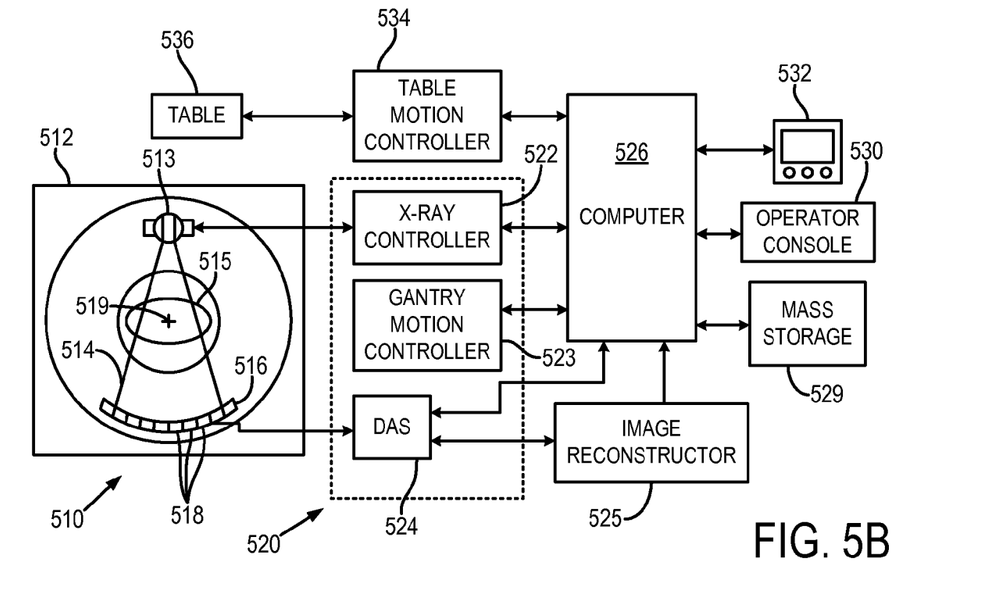
FIG. 5B is a block diagram of the CT imaging system of FIG. 5A.

The rotation of the gantry and the operation of the x-ray source 513 are governed by a control mechanism 520 of the CT system. The control mechanism 520 includes an x-ray controller 522 that provides power and timing signals to the x-ray source 513 and a gantry motor controller 523 that controls the rotational speed and position of the gantry 512. A data acquisition system ("DAS") 524 in the control mechanism 520 samples analog data from detector elements 518 and converts the data to digital signals for subsequent processing. An image reconstructor 525, receives sampled and digitized x-ray data from the DAS 524 and performs high speed image reconstruction. The reconstructed image is applied as an input to a computer 526 which stores the image in a mass storage device 528.

The computer 526 also receives commands and scanning parameters from an operator via console 530 that has a keyboard. An associated display 532 allows the operator to observe the reconstructed image and other data from the computer 526. The operator supplied commands and parameters are used by the computer 526 to provide control signals and information to the DAS 524, the x-ray controller 522 and the gantry motor controller 523. In addition, computer 526 operates a table motor controller 534 which controls a motorized table 536 to position the patient 515 in the gantry 512.

Figure 6:
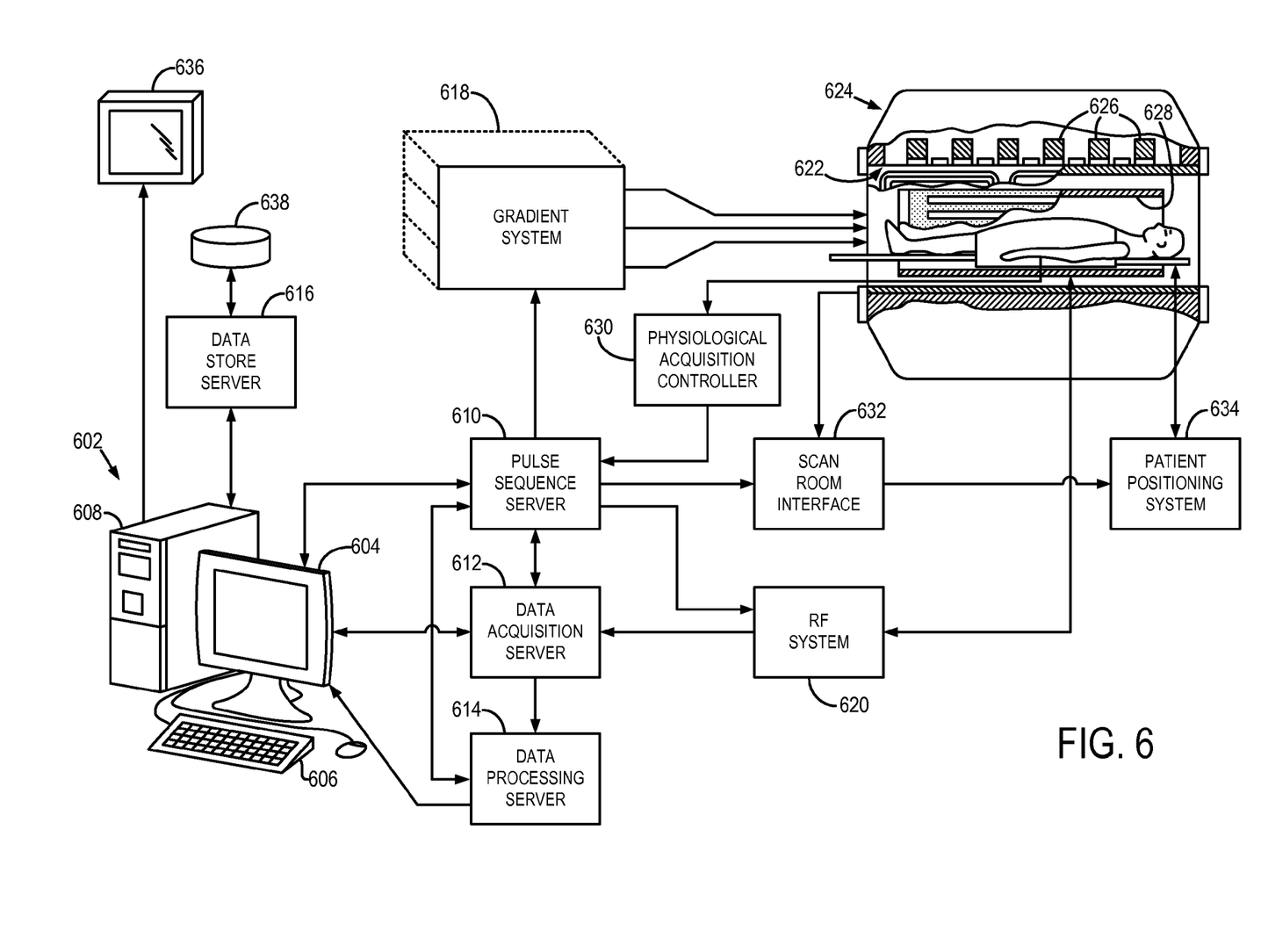
FIG. 6 is a block diagram of an exemplary magnetic resonance imaging ("MRI") system that employs the present invention.

Referring particularly now to FIG. 6, an exemplary magnetic resonance imaging ("MRI") system 600 is illustrated. The MRI system 600 includes a workstation 602 having a display 604 and a keyboard 606. The workstation 602 includes a processor 608, such as a commercially available programmable machine running a commercially available operating system. The workstation 602 provides the operator interface that enables scan prescriptions to be entered into the MRI system 600. The workstation 602 is coupled to four servers: a pulse sequence server 610; a data acquisition server 612; a data processing server 614, and a data store server 616. The workstation 602 and each server 610, 612, 614 and 616 are connected to communicate with each other.

The pulse sequence server 610 functions in response to instructions downloaded from the workstation 602 to operate a gradient system 618 and a radiofrequency ("RF") system 620. Gradient waveforms necessary to perform the prescribed scan are produced and applied to the gradient system 618, which excites gradient coils in an assembly 622 to produce the magnetic field gradients $G_x$, $G_y$, and $G_z$ used for position encoding MR signals. The gradient coil assembly 622 forms part of a magnet assembly 624 that includes a polarizing magnet 626 and a whole-body RF coil 628.

RF excitation waveforms are applied to the RF coil 628, or a separate local coil (not shown in FIG. 6), by the RF system 620 to perform the prescribed magnetic resonance pulse sequence. Responsive MR signals detected by the RF coil 628, or a separate local coil (not shown in FIG. 6), are received by the RF system 620, amplified, demodulated, filtered, and digitized under direction of commands produced by the pulse sequence server 610. The RF system 620 includes an RF transmitter for producing a wide variety of RF pulses used in MR pulse sequences. The RF transmitter is responsive to the scan prescription and direction from the pulse sequence server 610 to produce RF pulses of the desired frequency, phase, and pulse amplitude waveform. The generated RF pulses may be applied to the whole body RF coil 628 or to one or more local coils or coil arrays (not shown in FIG. 6).

The RF system 620 also includes one or more RF receiver channels. Each RF receiver channel includes an RF amplifier that amplifies the MR signal received by the coil 628 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \qquad (22);$$

and the phase of the received MR signal may also be determined:

$$\phi = \tan^{-1}\left(\frac{Q}{I}\right). \qquad (23)$$

The pulse sequence server 610 also optionally receives patient data from a physiological acquisition controller 630. The controller 630 receives signals from a number of different sensors connected to the patient, such as electrocardiograph ("ECG") signals from electrodes, or respiratory signals from a bellows or other respiratory monitoring device. Such signals are typically used by the pulse sequence server 610 to synchronize, or "gate," the performance of the scan with the subject's heart beat or respiration.

The pulse sequence server 610 also connects to a scan room interface circuit 632 that receives signals from various sensors associated with the condition of the patient and the magnet system. It is also through the scan room interface circuit 632 that a patient positioning system 634 receives commands to move the patient to desired positions during the scan.

The digitized MR signal samples produced by the RF system 620 are received by the data acquisition server 612. The data acquisition server 612 operates in response to instructions downloaded from the workstation 602 to receive the real-time MR data and provide buffer storage, such that no data is lost by data overrun. In some scans, the data acquisition server 612 does little more than pass the acquired MR data to the data processor server 614. However, in scans that require information derived from acquired MR data to control the further performance of the scan, the data acquisition server 612 is programmed to produce such information and convey it to the pulse sequence server 610. For example, during prescans, MR data is acquired and used to calibrate the pulse sequence performed by the pulse sequence server 610. Also, navigator signals may be acquired during a scan and used to adjust the operating parameters of the RF system 620 or the gradient system 618, or to control the view order in which k-space is sampled. The data acquisition server 612 may also be employed to process MR signals used to detect the arrival of contrast agent in a magnetic resonance angiography ("MRA") scan. In all these examples, the data acquisition server 612 acquires MR data and processes it in real-time to produce information that is used to control the scan.

The data processing server 614 receives MR data from the data acquisition server 612 and processes it in accordance with instructions downloaded from the workstation 602. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 614 are conveyed back to the workstation 602 where they are stored. Real-time images are stored in a data base memory cache (not shown in FIG. 6), from which they may be output to operator display 612 or a display 636 that is located near the magnet assembly 624 for use by attending physicians. Batch mode images or selected real time images are stored in a host database on disc storage 638. When such images have been reconstructed and transferred to storage, the data processing server 614 notifies the data store server 616 on the workstation 602. The workstation 602 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for enhancing signal-to-noise characteristics of an image, the steps of the method comprising:
    a) providing a previously reconstructed image to be enhanced;
    b) producing synthesized image data by performing a forward projection of the provided image;
    c) producing a prior image by filtering the provided image such that noise from the provided image is substantially suppressed in the prior image;
    d) subtracting the provided image and the prior image to produce a sparsified image;
    e) selecting an estimate image that is an estimate of an enhanced image having a higher signal-to-noise ratio than the provided image, wherein the estimate image is different than the provided image; and
    f) reconstructing the enhanced image by iteratively minimizing an objective function that includes a term containing the sparsified image and a term that includes a difference between a forward projection of the selected estimate image and the synthesized image data.

2. The method as recited in claim 1 in which the forward projection performed in step b) is at least one of a Radon transformation, a Fourier transformation, and a wavelet transformation.

3. The method as recited in claim 1 in which step c) includes applying a low pass filter to the provided image.

4. The method as recited in claim 1 in which step a) includes acquiring image data with an imaging system and reconstructing an image from the acquired image data.

5. The method as recited in claim 4 in which the imaging system is at least one of an x-ray imaging system, an x-ray computed tomography system, a C-arm x-ray imaging system, an x-ray tomosynthesis imaging system, a projection x-ray imaging system, a magnetic resonance imaging system, a positron emission tomography system, a single photon emission computed tomography system, an ultrasound imaging system, and an optical imaging system.

6. The method as recited in claim 1 in which step b) includes resampling the provided image before performing the forward projection of the provided image.

7. The method as recited in claim 6 in which resampling the provided image includes oversampling the provided image.

8. The method as recited in claim 1 in which the minimization performed in step f) is a constrained minimization.

9. The method as recited in claim 8 in which the constrained minimization is constrained by a consistency condition.

10. The method as recited in claim 1 in which the objective function has at least one additional term that includes the selected estimate image.

11. A method for reconstructing an image of a subject using a medical imaging system, the steps of the method comprising:
    a) acquiring, with the medical imaging system, image data from the subject;
    b) reconstructing from the acquired image data, a first image of the subject;
    c) producing a prior image from the first image by filtering the first image so that noise from the first image is substantially suppressed in the prior image;
    d) producing synthesized image data from the first image by forward projecting the first image;
    e) producing a sparsified image by subtracting the prior image and the first image;
    f) selecting an estimate image that is an estimate of a target image of the subject having a higher signal-to-noise ratio than the first image, the estimate image being different than the first image; and
    g) reconstructing the target image of the subject by iteratively minimizing an objective function that includes a term containing the sparsified image and a term that includes a difference between a forward projection of the selected estimate image and the synthesized image data.

12. The method as recited in claim 11 in which the medical imaging system includes at least one of an x-ray imaging system, an x-ray computed tomography system, a C-arm x-ray imaging system, an x-ray tomosynthesis imaging system, a projection x-ray imaging system, a magnetic resonance imaging system, a positron emission tomography system, a single photon emission computed tomography system, an ultrasound imaging system, and an optical imaging system.

13. The method as recited in claim 11 in which the forward projection performed in step d) is at least one of a Radon transformation, a Fourier transformation, and a wavelet transformation.

14. The method as recited in claim 11 in which the objective function has at least one additional term that includes the selected estimate image.

* * * * *